(12) United States Patent
Sirhan et al.

(10) Patent No.: US 6,569,180 B1
(45) Date of Patent: May 27, 2003

(54) CATHETER HAVING EXCHANGEABLE BALLOON

(75) Inventors: Motasim Sirhan, Sunnyvale, CA (US); John Yan, Los Gatos, CA (US); Kevin Gertner, Los Gatos, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 19 days.

(21) Appl. No.: 09/585,943

(22) Filed: Jun. 2, 2000

(51) Int. Cl.[7] ............................................. A61M 25/10
(52) U.S. Cl. ..................... 606/194; 606/195; 623/1.11; 604/103
(58) Field of Search ................. 606/194, 195, 606/192, 193, 196; 604/101.04, 101.05, 103; 623/1.11

(56) References Cited

U.S. PATENT DOCUMENTS

| | | | |
|---|---|---|---|
| 4,573,966 A | * | 3/1986 | Weikl et al. ............. 604/53 |
| 4,655,746 A | | 4/1987 | Daniels et al. |
| 4,748,982 A | | 6/1988 | Horzewski et al. |
| 4,762,129 A | | 8/1988 | Bonzel |
| 4,911,163 A | * | 3/1990 | Fina ........................ 606/127 |
| 4,947,864 A | | 8/1990 | Shockey et al. |
| 4,988,356 A | | 1/1991 | Crittenden et al. |
| 5,040,548 A | | 8/1991 | Yock |
| 5,061,273 A | | 10/1991 | Yock |
| 5,135,535 A | | 8/1992 | Kramer |
| 5,180,367 A | * | 1/1993 | Kontos et al. ............. 604/101 |
| 5,195,978 A | | 3/1993 | Schiffer |
| 5,232,445 A | | 8/1993 | Bonzel |
| 5,263,963 A | | 11/1993 | Garrison et al. |
| 5,281,203 A | | 1/1994 | Ressemann |
| 5,300,085 A | | 4/1994 | Yock |
| 5,328,472 A | | 7/1994 | Steinke et al. |
| 5,334,147 A | | 8/1994 | Johnson |
| 5,336,184 A | | 8/1994 | Teirstein |
| 5,346,505 A | | 9/1994 | Leopold |
| 5,350,395 A | | 9/1994 | Yock |
| 5,364,376 A | | 11/1994 | Horzewski et al. |
| 5,380,283 A | | 1/1995 | Johnson |
| 5,383,853 A | | 1/1995 | Jung et al. |
| 5,395,335 A | | 3/1995 | Jang |
| 5,413,559 A | | 5/1995 | Sirhan et al. |
| 5,451,233 A | | 9/1995 | Yock |
| 5,458,613 A | | 10/1995 | Gharibadeh et al. |
| 5,460,185 A | | 10/1995 | Johnson et al. |
| 5,462,529 A | | 10/1995 | Simpson et al. |
| 5,468,225 A | | 11/1995 | Teirstein |
| 5,472,425 A | | 12/1995 | Teirstein |
| 5,501,227 A | | 3/1996 | Yock |
| 5,531,690 A | | 7/1996 | Solar |

(List continued on next page.)

FOREIGN PATENT DOCUMENTS

| | | | |
|---|---|---|---|
| RU | 627828 | * | 10/1978 |
| WO | WO 97/07756 | | 3/1997 |
| WO | WO 99/13935 | | 2/1999 |

*Primary Examiner*—Michael H. Thaler
(74) *Attorney, Agent, or Firm*—Townsend and Townsend and Crew LLP (57) ABSTRACT

An intravascular balloon catheter comprises a tubular catheter body having a balloon structure removably mounted over the catheter body. The catheter body has a guidewire lumen, and the catheter body may be left in place within a patient's vasculature while the balloon structure is withdrawn and optionally a second balloon structure introduced over the catheter body. The catheter and methods of the present invention are particularly suitable for performing angioplasty and subsequent procedures, such as stent placement, which are best performed using successive interventional balloon structures.

14 Claims, 10 Drawing Sheets

U.S. PATENT DOCUMENTS

| | | | |
|---|---|---|---|
| 5,533,968 A | 7/1996 | Muni et al. | |
| 5,545,134 A | 8/1996 | Hilaire et al. | |
| 5,554,118 A | 9/1996 | Jang | |
| 5,571,094 A | 11/1996 | Sirhan | |
| 5,607,406 A | 3/1997 | Hernandez et al. | |
| 5,620,417 A | 4/1997 | Jang et al. | |
| 5,626,600 A | 5/1997 | Horzewski et al. | |
| 5,685,312 A | 11/1997 | Yock | |
| 5,709,658 A | 1/1998 | Sirhan et al. | |
| 5,728,067 A | 3/1998 | Enger | |
| 5,738,667 A | 4/1998 | Solar | |
| 5,749,888 A | 5/1998 | Yock | |
| 5,755,685 A | 5/1998 | Andersen | |
| 5,769,868 A | 6/1998 | Yock | |
| 5,776,141 A | 7/1998 | Klein et al. | |
| 5,800,391 A * | 9/1998 | Kontos et al. | 604/96 |
| 5,807,355 A | 9/1998 | Ramzipoor et al. | |
| 5,810,869 A | 9/1998 | Kaplan et al. | |
| 5,814,061 A | 9/1998 | Osborne et al. | |
| 5,827,241 A | 10/1998 | Douk et al. | |
| 5,830,227 A | 11/1998 | Fischell et al. | |
| 5,833,659 A | 11/1998 | Kranys | |
| 5,846,246 A | 12/1998 | Dirks et al. | |
| 5,891,056 A | 4/1999 | Ramzipoor | |
| 5,919,164 A | 7/1999 | Andersen | |
| 5,919,175 A | 7/1999 | Sirhan | |
| 5,921,971 A | 7/1999 | Agro et al. | |
| 5,944,691 A | 8/1999 | Querns et al. | |
| 5,947,927 A | 9/1999 | Mertens | |
| 5,980,486 A | 11/1999 | Enger | |
| 6,007,517 A | 12/1999 | Anderson | |
| 6,048,484 A | 4/2000 | House et al. | |
| 6,056,722 A | 5/2000 | Jayaraman | |
| 6,168,579 B1 | 1/2001 | Tsugita | |
| 6,196,995 B1 | 3/2001 | Fagan | |
| 6,200,305 B1 | 3/2001 | Berthiaume et al. | |
| 6,299,595 B1 | 10/2001 | Dutta et al. | |

* cited by examiner

CATHETER HAVING EXCHANGEABLE BALLOON

BACKGROUND OF THE INVENTION

1. Field of the Invention

The present invention relates generally to medical devices and methods. More particularly, the present invention relates to a balloon catheter having an exchangeable balloon structure.

Percutaneous transluminal angioplasty procedures have become a therapy of choice for treating stenosed regions in the patient's vasculature, particularly the coronary vasculature. Recently, the use of such angioplasty procedures has often been combined with stent placement and/or radiation treatment to inhibit restenosis and hyperplasia following angioplasty. When performing such multiple, sequential treatments, it is usually necessary to "exchange" catheters which are used to perform each of the procedures. That is, the initial angioplasty treatment will be performed using a balloon angioplasty catheter. After the angioplasty is completed, a second catheter carrying a stent or other vascular prosthesis must then be introduced to the treatment site. Introduction of the second catheter involves first removing the balloon angioplasty catheter and then placing the second catheter in the treatment region. Optionally, a third catheter may then be exchanged for the second in order to perform radiation or other treatments in order to inhibit hyperplasia.

In performing such multiple, sequential treatments, most physicians prefer to leave a "guidewire" in place to the treatment location. A guidewire is a small diameter, highly flexible wire that can be steered to the target location through the vasculature and which then acts as a guide path for introducing and positioning the balloon angioplasty and other interventional catheters.

In the early days, balloon angioplasty catheters were designed to be introduced into the vasculature in an "over-the-wire" manner. That is, the catheters were designed to have passages, commonly referred to as guidewire lumens, which extended the entire distance from the distal end of the catheter to the proximal end of the catheter. The catheter could then be loaded over a proximal end of a guidewire which was already in place in the patient and then advanced over the guidewire until a distal end of the catheter reached the target site. While functional, the need to maintain control of the guidewire while the interventional catheter was being introduced meant that the guidewire had to have an excess length outside of the patient which was greater than the length of the catheter being introduced. If the length were any shorter, the treating physician would not be able to hold on to the guidewire as the catheter was being introduced. Although necessary for catheter introduction, the excess guidewire length (optionally in the form of a detachable extension) was very difficult to manage during other parts of the treatment.

To overcome the difficulties associated with very long guidewires "rapid exchange" or "monorail" balloon angioplasty catheters were developed. A number of specific designs have been developed over the years, and the rapid exchange catheters generally have a shortened guidewire lumen which extends from a distal tip of the catheter to an exit port located closer to the distal end of the catheter than to the proximal end. By reducing the length of the guidewire lumen, the need for a guidewire having excess length outside of the patient is also reduced.

The use of rapid exchange catheters has become wide spread, and they have proven to be particularly valuable for use as stent delivery catheters. Stent delivery catheters are normally used after an initial angioplasty treatment. In such cases, the angioplasty catheter will be removed and exchanged for the stent delivery catheter. Use of an angioplasty catheter having a rapid exchange design facilitates removal of the angioplasty catheter over short guidewires. Similarly, use of the stent delivery catheter having a rapid exchange design facilitates introduction of the catheter over the guidewire which remains in place in the patient.

Despite their widespread acceptance, rapid exchange catheters suffer from a number of limitations. In particular, the shortened guidewire lumens reduce the "pushability" of the rapid exchange catheters. The use of full length guidewire lumens as provided by the over-the-wire designs results in an overall increase in the column strength of the catheter being introduced. That is, the catheter derives column strength not only from the catheter body itself, but also from the guidewire which is in place in the guidewire lumen over the entire length of the catheter, allowing better access across tight lesions. Additionally, presence of the guidewire in a full length guidewire lumen lessens the risk of the catheter body kinking or collapsing in tortuous regions of the vasculature. Kinking can be a particular problem at the point where the guidewire exits a catheter body in a rapid exchange design.

The second problem associated with the use of rapid exchange catheters is the inability to exchange the guidewire. Guidewire exchange in over-the-wire catheters is quite simple since the guidewire lumen extends the full length of the catheter body. In rapid exchange catheters, in contrast, there is no guidewire lumen in the proximal portions of the angioplasty catheter. It is therefore difficult to reintroduce a guidewire into the shortened guidewire lumen of the rapid exchange catheter.

For these reasons, it would be desirable to provide improved apparatus, methods, and kits which permit the exchange of catheters and catheter components over shortened guidewires. Particularly, it would be desirable to provide improved balloon angioplasty and other catheters which can be introduced to the vasculature in the manner of an over-the-wire catheter, but which allow removal of the catheter over a shortened guidewire and/or which permits exchange of catheter components over the catheter body which remains in place over the guidewire. It would be further desirable to provide balloon catheters and methods for their use which permit exchange of balloon structures over the catheter body while the catheter body remains in place in the vasculature over a guidewire and where the replacement balloon structure may optionally carry a stent. At least some of these objectives will be met by the invention described in claims herein after.

2. Description of the Background Art

Rapid exchange catheters having guidewire exchange devices are described in U.S. Pat. Nos. 5,281,203; 5,571,094; and 5,919,175. Sleeves for positioning stents, drug infusion tubes, imaging transducers, and other interventional devices over balloon angioplasty catheters are described in U.S. Pat. Nos. 5,776,191; 5,810,869; and PCT Publication W097/07756. Rapid exchange and related catheters are described in U.S. Pat. Nos. 6,056,722; 6,007,517; 5,980,4861; 5,947,927; 5,921,971; 5,919,164; 5,891,056; 5,846,246; 5,833,659; 5,830,227; 5,827,241; 5,807,355; 5,814,061; 5,769,868; 5,855,685; 5,749,888; 5,738,667; 5,728,067; 5,709,658; 5,685,312; 5,626,600; 5,620,417; 5,607, 406; 5,554,118; 5,545,134; 5,531,690; 5,501,227; 5,472,425; 5,468,225; 5,460,185; 5,458,613; 5,451,223; 5,413,559; 5,395,335; 5,383,853; 5,364,376; 5,350,395; 5,346,505; 5,336,184; 5,334,147; 5,328,472; 5,300,085; 5,380,283; 5,263,963; 5,232,445; 5,195,978; 5,135,535; 5,061,273; 5,040,548; 4,762,129; 4,988,356; 4,947,864; 4,748,982; and WO 99/13935.

SUMMARY OF THE INVENTION

The present invention provides improved intravascular balloon catheters and methods for their use. The catheters are suitable for use for the treatment of a variety of conditions within different locations of a patient's vasculature. In particular, the catheters can be used in the coronary, peripheral, and cerebral regions of a patient's vasculature for virtually any treatment modality that relies on balloon expansion, particulaty angioplasty, stent placement, and the like.

Intravascular balloon catheters according to present invention comprise a tubular catheter body having a proximal end, a distal end, and a guidewire lumen extending therebetween. Usually, the guidewire lumen will extend the entire distance from the proximal end to the distal end of the catheter, although in some instances the guidewire lumen could be shortened (in manner of a conventional rapid exchange catheter), could be split to facilitate removal of the guidewire, and/or could be provided with a breakaway feature which allows opening the guidewire lumen to facilitate guidewire removal. In all cases, the intravascular balloon catheters of the present invention will further comprise a balloon structure having a passage which is slidably receivable over the tubular catheter body. Thus, the balloon structure can be selectively introduced and removed over the tubular catheter body to permit exchange of the balloon structure with another balloon structure (or in some cases a non-balloon structure) either before or during performance of an intravascular interventional procedure employing the balloon.

Usually, the balloon structure will comprise an inflatable component, e.g. a balloon, having an inflation tube extending proximally from the balloon when the balloon is disposed near the distal end of the tubular catheter body. Conveniently, the inflation tube can also be used to manipulate the balloon structure. That is, the balloon structure can be advanced and withdrawn over the tubular catheter body by pushing and pulling on a proximal end of the inflation tube while the tubular catheter body remains in place. In such cases, the inflation tube will have sufficient column strength to advance and retract the balloon structure over the tubular catheter body. Usually, it will be in the form of a hypotube, but other structures would also be possible. Alternatively, a separate manipulation shaft could be attached to the balloon structure with a separate inflation structure, either attached directly to the balloon structure or optionally provided in the tubular catheter body. In the later case, the tubular catheter body will include an inflation lumen and the balloon structure will include an inflation port which mates with the inflation lumen in order to permit inflation of the balloon through the tubular catheter body. A separate manipulation shaft will then be provided on the balloon structure extending proximally from the balloon structure when the balloon is disposed near the distal end of the tubular catheter body.

The inflatable structure, in an exemplary embodiment, will comprise a balloon attached to an inner sleeve, where the inner sleeve has an axial passage which removably receives the tubular catheter body. Usually, the inner sleeve will be longer than the balloon structure, with the inner sleeve usually having a length in the range from 3 cm to 50 cm, usually from 4 cm to 40 cm, and typically from 5 cm to 25 cm. The balloon or other inflatable structure (or in some cases other radially expansible structure) will be much shorter, typically being in the range from 1 cm to 5 cm, usually from 2 cm to 4 cm. The inner sleeve may be formed from conventional catheter materials, typically being an extruded polymer tube.

When an inflation tube is attached to the balloon structure, the tubular catheter body will preferably be free from structure which interferes with introduction of the balloon structure over the proximal end of the tubular catheter body. Optionally, a hemomostatis structure may be provided within the proximal end of the guidewire lumen, but the hemomostatis structure will not add to the profile of or otherwise affect the catheter body such that it would interfere with loading of the balloon structure. Alternatively, a removable hub could be provided, but upon removal of the hub, the proximal end of tubular catheter body should be sufficiently free of protruding structure to permit introduction of the balloon structure thereover. When the inflation lumen is provided within the tubular catheter body, it will be usually be necessary to provide a removable hub at the proximal end of the catheter body to permit inflation of the balloon through a port on the hub.

The intravascular balloon catheters of the present invention will include at least a first balloon structure having the properties described above. Usually, the first balloon structure will be preloaded over the tubular catheter body, and the assembly sterilized and packaged as a complete unit. Optionally, a second balloon structure having a passage which is slidably receivable over the tubular catheter body may be also provided. The second balloon structure may be included as part of a single system together with the first balloon structure and tubular catheter body, usually being packaged together in a sterile manner with the other system components. Typically, the second balloon structure will differ from the first in someway, such as the dimensions, including diameter, length, or both; shape; balloon material; balloon characteristics, such as compliance, flexibility, elasticity or the like; or other feature. In a particular example, the second balloon structure may carry a stent or other vascular prosthesis, where the first balloon structure is intended for performing angioplasty or other therapeutic or diagnostic procedure, and the second balloon structure is intended to deliver a stent after the angioplasty treatment. Other examples include drug infusion balloons, radioactive delivery balloons, atherectomy, and the like. Of course, the intravascular balloon catheters including only a single balloon structure may also be adapted to carry a stent, drug infusion balloon, radioactive delivery balloon, or the like, as well.

Methods according to the present invention for balloon exchange over a tubular catheter body comprise withdrawing a balloon structure coaxially over the tubular catheter body while the tubular catheter body remains in place over a guidewire in a blood vessel. The balloon structure is withdrawn proximally, usually so that it may be removed over a proximal end of the tubular end of the catheter body. After withdrawing a first balloon structure, a second balloon structure is introduced over the tubular catheter body in distal direction while the tubular catheter body remains in place over the guidewire. Typically, the second balloon structure will be introduced over the proximal end of the tubular catheter body. A particular advantage of the these methods is that the first balloon structure and tubular catheter body maybe introduced over a short guidewire (i.e. one that is only slightly longer than the angioplasty catheter itself e.g. 10 cm to 35 cm) in the manner of an over-the-wire angioplasty catheter. After the balloon catheter assembly is in place, however, the first balloon structure may be withdrawn from over the proximal end of the tubular catheter body and exchanged for a second (subsequent) balloon structure. As the balloon structures themselves will be shorter than the catheter body, typically being from 3 cm to 50 cm, they can be withdrawn without losing manual access to the proximal ends of the tubular catheter body and short guidewire.

In an exemplary protocol using the intravascular balloon catheters and methods of the present invention, the balloon catheter comprising a first balloon structure pre-loaded over a tubular catheter body is first introduced together with a guidewire to a target region in the vasculature in a conventional manner. Usually, a distal end of the guidewire, extends beyond the distal end of the tubular catheter body by a short distance as the balloon catheter assembly is being advanced. In that way, a short guidewire can be used where the guidewire is fully supported in the guidewire lumen of the tubular catheter body, which typically runs the entire length of the catheter body.

After the first balloon structure has been positioned at the target location within the vasculature, e.g. a stenosed region within the coronary vasculature, the first balloon may be expanded to treat the target region, e.g. by opening the stenosed region. Thus, the first balloon structure may act as angioplasty balloon, with the balloon being substantially non-distensable at the relatively high inflation pressure is used, typically from 3 atmospheres to 20 atmospheres. Alternatively, the first balloon could be any other therapeutic or diagnostic-type of balloon.

After the initial balloon treatment is completed, the balloon structure may be withdrawn proximally from over the tubular catheter body. This may be accomplished by using the inflation tube when the balloon structure includes such an inflation tube. Otherwise, withdrawal will be typically be accomplished using a shaft, such as a solid core wire or hypotube attached to the balloon structure and extending proximally therefrom. The passage of the balloon structure, as described above, will usually be relatively short so that the balloon structure may be withdrawn from over the proximal end of the tubular catheter body and guidewire, with the lengths of the tubular catheter body and guidewire being extended a small amount to allow manual access while the balloon structure is being withdrawn thereover.

After the first balloon structure has been withdrawn, the second balloon structure may be introduced over the proximal ends of both the guidewire and the tubular catheter body. Again, the length of the passage in the second balloon structure will typically be in the range from about 3 cm to 50 cm, so that manual access to both the tubular catheter body and guidewire will remain at all times. The second balloon structure may be advanced using either an inflation tube or other manipulation shaft overextending proximally from the balloon structure. The balloon structure will then be advanced until it reaches a location near the distal end of the tubular catheter body where it can be further positioned within the treatment region. In the exemplary case, the second balloon structure will carry a balloon expandable stent or other vascular prosthesis, where the stent is implanted by expansion of the second balloon structure, Optionally, further treatments can be provided, e.g. using a third coaxial sleeve structure which could carry drugs, genes, radiation, or other therapeutic agents or modalities. The third coaxial structure may, but need not, also comprise an inflatable balloon. The third structure usually will be introduced in a manner analogous to the introduction of the second balloon structure, as just described. There, of course, could be fourth, fifth, and even more treatment steps performed by successively introducing balloon, sleeve, and other structures over the tubular catheter body. Moreover, it will also be possible to introduce two or more balloon structures over the tubular catheter body at the same time.

After the patient treatment is completed, the intravasculature catheter structure which remains over the guidewire will be withdrawn. In a first option, the catheter and guidewire can be withdrawn simultaneously where the catheter is never in the vasculature without the guidewire present in the guidewire lumen. Alternatively, the balloon or other coaxial sleeve structure can be withdrawn from over the tubular catheter body prior to removing the tubular catheter body and guidewire simultaneously. As a third option, the tubular catheter body could be provided with an axial slit or break away portion to permit removal of the tubular catheter body from over the guidewire with the guidewire remaining in place. In that way the guidewire would remain in place for subsequent use with other catheters or devices.

DESCRIPTION OF THE SPECIFIC EMBODIMENTS

Intravascular balloon catheter 10 constructed in accordance with the principles of the present invention is illustrated in FIGS. 1–5. The intravascular balloon catheter 10 comprises a tubular catheter body 12 and a balloon structure 14. The tubular catheter body 12 is an elongated structure having a proximal end 16, a distal end 18, and a guidewire lumen 20 (FIG. 5) extending therebetween. Optionally, a tapered cone 22 or other distal structure may be provided at the distal end 18 in order to facilitate introduction of the catheter body through the vasculature.

Tubular catheter body 12 will have dimensions selected to accomodate the particular target location within the vasculature to be treated. Usually the tubular catheter body will have a length in the range from 100 cm to 200 cm, typically 125 cm to 150 cm for treatment of the coronary vasculature. The outer diameter of the tubular catheter body will also be chosen depending on the intended use, with catheter bodies typically having a diameter in the range from 1 French (F; 0.33 mm) to 10 F, typically from 2 F to 5 F. The diameter of the guidewire lumen will be selected to receive a conventional coronary or other guidewire. Such guidewires typically have diameters of 0.01 inch (0.25 mm) to 0.035 inch (0.9 mm) and the corresponding guidewire lumens will typically have diameters in the range from 0.3 mm to 2 mm, usually from or 0.4 mm to 0.6 mm, respectively.

The tubular catheter body may be formed from conventional catheter materials, typically from hypotube or as extrusions of polymeric resins. Suitable resins materials include polyamides (nylons) polyimides, polyvinylchloride, PBAX, PTFE, and the like. Catheter bodies may optionally be reinforced with braids, coils, filaments or other materials in order to enhance the pushability and/or reduce the wall thickness. The tapered distal tip 22 may be formed integrally with the remainder of the catheter body 12 or may be formed separately and attached using adhesives, heat fusion, or other techniques. In some instances, the tip 22 may be formed from a particularly soft material in order enhance a traumatic introduction of the catheter.

Figure 5:
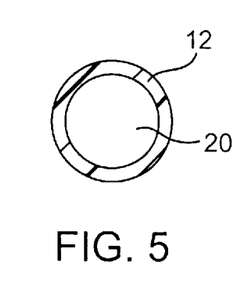
FIG. 5 is a cross-sectional view taken along line 5—5 of FIG. 2.
Figure 5A:
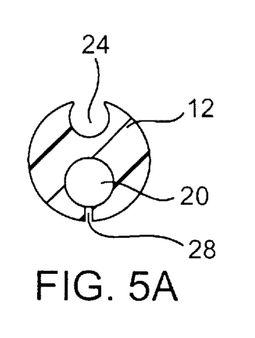
FIG. 5A is an alternative cross-sectional view taken along line 5—5 of FIG. 2.
Figure 6:
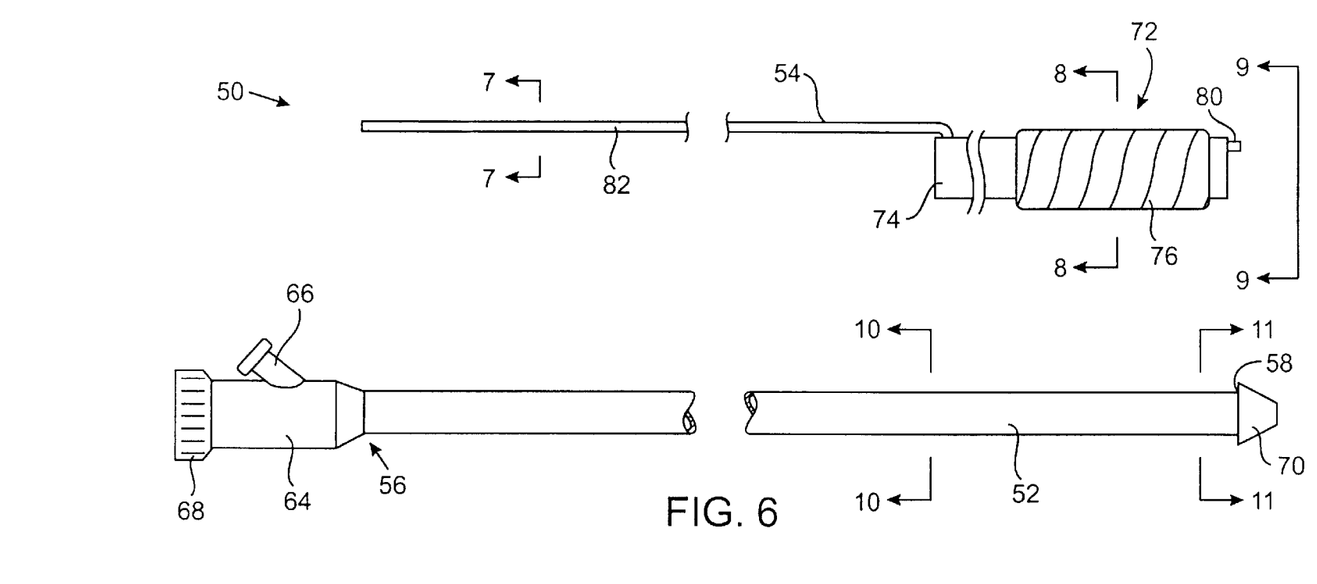
FIG. 6 illustrates an alternative embodiment of the intravascular balloon catheter of the present invention, shown with the tubular catheter body and first balloon structure separated from one another.

In a first alternative construction, as shown in FIG. 5A, tubular catheter body 12 may include an axial slot 24 to removably receive an inflation tube 26 which is attached at the proximal end of the balloon structure 14. Inclusion of the slot 24 can reduce the overall diameter (profile) of the catheter. As a second alternative, the guidewire lumen 20 in FIG. 5A, can have an axial slit 28 which permits withdrawal of the guidewire from the lumen 20 as the catheter is withdrawn from the patient. In place of slit 28, the tubular catheter body 12 could be provided with a frangible "break way" structure to permit opening of the lumen as the catheter is withdrawn and the guidewire removed.

The balloon structure 14 comprises the inflation tube 26 having an inflation lumen 29 (FIG. 3) extending axially therethrough. A Luer or other connector 30 is attached to a proximal end 32 of the inflation tube 26, and a balloon assembly 34 is attached at the distal end 36. The balloon structure 14 further comprises an inner sleeve 38 and an inflatable balloon 40 attached over an outer surface of the inner sleeve. The inner sleeve has a central passage 41 having a diameter which is large enough to be introduced over the catheter body, usually being from 0.4 mm to 4 mm, more usually from 0.8 mm to 2 mm. The inner sleeve 38 is usually a single lumen tube, but in other embodiments could be a multiple lumen tube where only one of the lumens is intended to receive the tubular catheter body 12. Other lumens could be provided for perfusion or other purposes.

Figure 1:
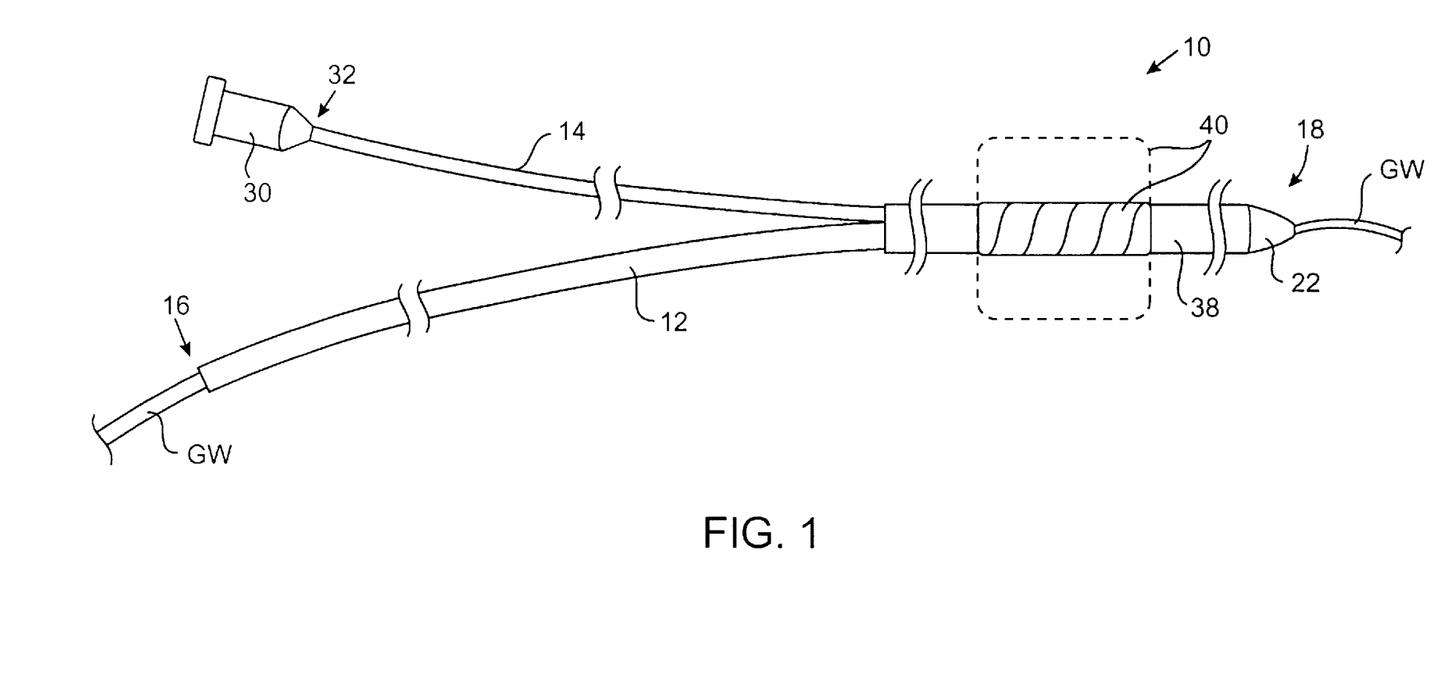
FIG. 1 illustrates an intravascular catheter comprising a tubular catheter body and a first balloon structure mounted over the catheter body and constructed in accordance with the principles of the present invention.
Figure 2:
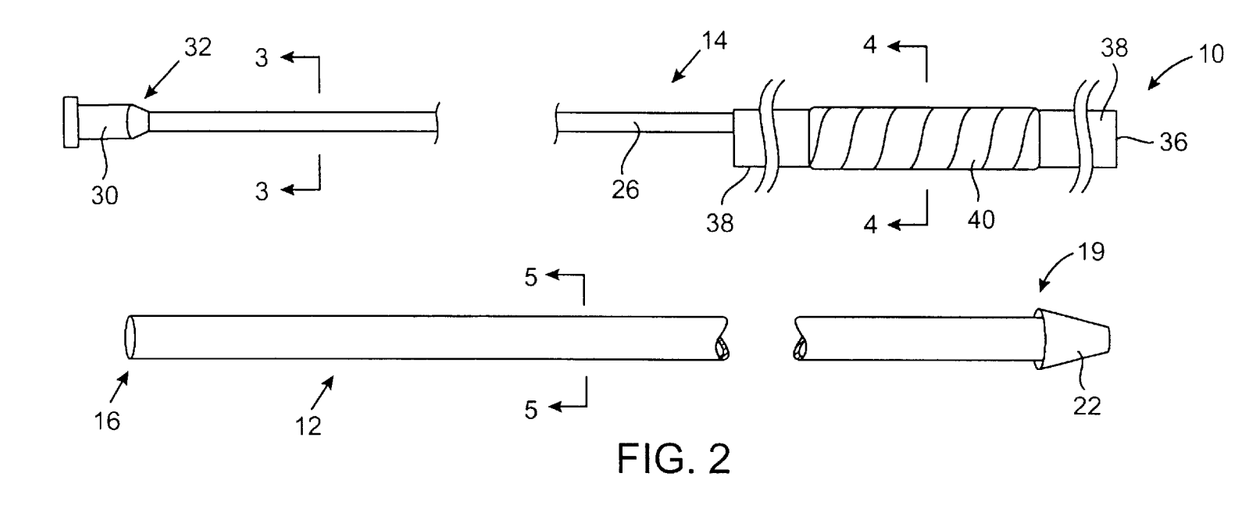
FIG. 2 illustrates the intravascular balloon catheter of FIG. 1 shown with the first balloon structure separated from the tubular catheter body.
Figure 3:
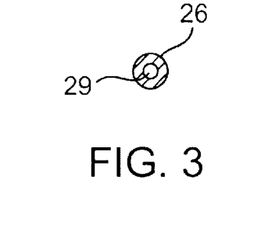
FIG. 3 is a cross-sectional view taken along line 3—3 of FIG. 2.
Figure 4:
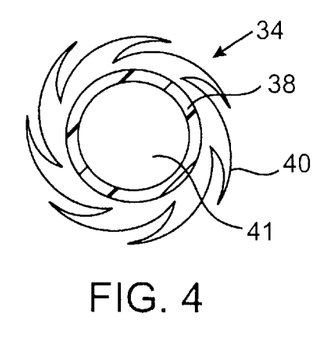
FIG. 4 is a cross-sectional view taken along line 4—4 of FIG. 2.

The balloon 40 is initially folded over the inner sleeve 38, as shown in full line in both FIGS. 1 and 2. The balloon may be inflated by introduction of a suitable inflation medium through the inflation tube 14 to produce an inflated configuration, as shown in broken line in FIG. 1. The dimensions, materials, and other characteristics of the balloon 40 maybe as generally described in the patent and medical literature for angioplasty balloons.

Alternatively, the balloon 40 may be configured for purposes other than or in addition to angioplasty. For example, the balloon 40 may be configured to receive a stent or other balloon expandable vascular prosthesis thereover. Such vascular prostheses include both stents and graft structures, usually intended to maintain patency of a blood vessel following angioplasty. The stents which may be delivered using the balloon structures of the present inventions will usually be of the malleable or deformable type, where the stent is initially in a narrow dimension to facilitate intraluminal delivery. After placement at the target site, the stent or graft is then expanded in situ by internal inflation of the balloon 40, causing expansion of the stent or graft structure in order to maintain radial expansion after the balloon is removed. Such balloon expandable stents and grafts are well-described in the patent and medical literature. See, for example, U.S. Pat. Nos. 4,733,665; 4,776,377; 4,877,030; 5,019,090; 5,102,417; 5,123,917; 5,195,984; 5,219,355; 5,344,426; 5,360,443; 5,382,261; 5,733,303; and 5,792,018, the full disclosures of which are incorporated herein by reference.

While the present invention will usually employ a conventional inflatable balloon as part of the balloon structure, it will also be possible to incorporate other radially expansible devices which are generally recognized in the art to be equivalent to inflatable balloons for the purpose of performing angioplasty and other intravascular interventional procedures. Such "balloon equivalents" include expansible shafts, expansible cages, modified balloons (such as half balloons, balloons with channels, etc.), malecots, and the like. Specific alternative structures are taught in U.S. Pat. Nos. 5,944,691; 5,533,968; and 6,048,484, the full disclosures of which are taught herein by reference.

It will be appreciated that, due to their modular nature, the intravascular balloon catheters 10 of the present invention may include more than one balloon structure, where the different balloon structures are often intended for different purposes. In a first particular example, the intravascular balloon catheters may include a first balloon structure intended for angioplasty and a second balloon structure 14 intended for stent placement. In the later case, the second balloon structure will usually have the stent preloaded over the balloon. Alternatively, of course it will be possible crimp the stent over the balloon immediately prior to use (i.e. in the hospital rather than at the point of manufacturing).

Referring to FIGS. 6–11, an alternative intravascular balloon catheter 50 constructed in accordance with the principles of the present inventions will be described. Intravascular balloon catheter 50, comprises a tubular catheter body 52 and a balloon structure 54. The tubular catheter body 52 has a proximal end 56, a distal end 58, and a guidewire lumen 60 (FIGS. 10 and 11) therethrough. In contrast to tubular catheter body 12 of intravascular balloon catheter 10, the tubular catheter body 52 of the second embodiment also includes a balloon inflation lumen 62 extending the entire length from proximal end 56 to distal end 58 thereof. To introduce both the guidewire through the guidewire lumen 60 and an inflation medium through the inflation lumen 62, a proximal hub 64 is removably attached to the proximal end 56 of the tubular catheter body 52. The hub includes both an inflation port 66 and a guidewire port 68, typically in the form of a hemostasis valve. The proximal hub 64 will be removable in order to permit introduction of the balloon structure 54 there-over. Specific designs for removable catheter hubs which are able to connect to inflation lumens are provided in U.S. Pat. No. 5,810,869, the full disclosure of which is incorporated herein by reference. A tapered distal nosecone 70 may optionally be mounted at the distal end 58 of the catheter body 52. The nosecone 70 may be similar nosecone 22 described in the earlier embodiment.

The balloon structure 54 comprises a balloon assembly 72 including an inner sleeve 74 having a balloon 76 disposed thereover. Inflation of the balloon 76 is provided through inflation lumen 62 in the tubular catheter body 52. Inflation lumen 62 terminates in a port 78 (FIG. 11) formed on a proximal surface of the nosecone 70. A connector 80 on the balloon assembly 72 mates with the port 78 when the balloon is properly positioned at the distal end of the tubular catheter body 52. An inflation medium introduced through the lumen 62 will reach the balloon in order to inflate the balloon.

Figure 7:
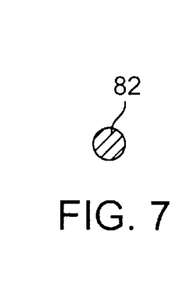
FIG. 7 is a cross-sectional view taken along line 7—7 of FIG. 6
Figure 8:
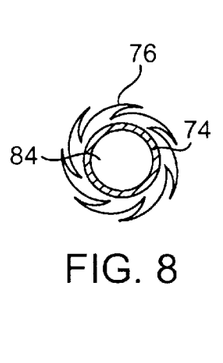
FIG. 8 is a cross-sectional view taken along line 8—8 of FIG. 6.
Figure 9:
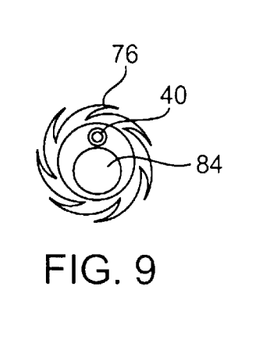
FIG. 9 is an end view taken along line 9—9 of FIG. 6.
Figures 10, 11:
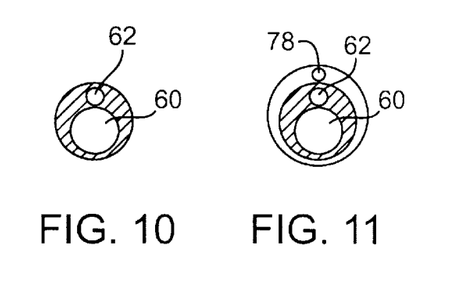
FIG. 10 is a cross-sectional view taken along the line 10—10 of FIG. 6.
FIG. 11 is a cross-sectional view taken along the line 11—11 of FIG. 6.

The balloon structure 54 further includes a shaft 82 which is attached to a proximal end of the inner sleeve 74 and which extends proximally there- from. Since the shaft is not needed for inflation, it can have a solid core as shown in FIG. 7. The shaft 82, however, will be sufficiently long and will have sufficient column strength in order to introduce a passage 84 of the balloon structure 54 over the tubular catheter body 52. The proximal hub 64 can be removed whenever the lumen assembly 72 of the balloon structure 54 is to be introduced over or withdrawn over the proximal end 56 of the tubular catheter body 52. At all other times, the proximal hub 54 may be placed over the proximal end of the catheter body in order to provide hemostasis for the guidewire as well as permit connection of the inflation source (not shown) to the balloon 76.

Figure 12:
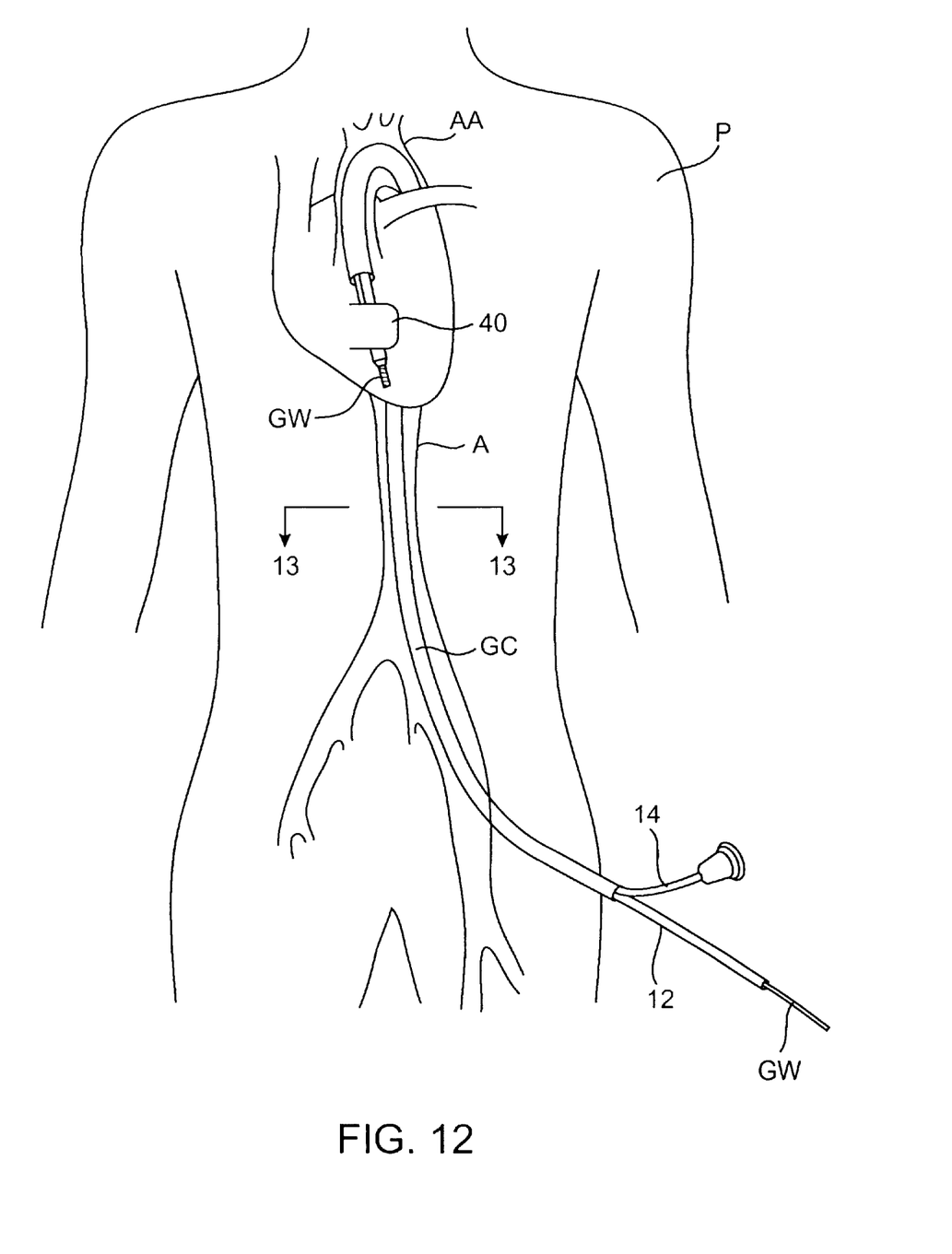
FIG. 12 is a schematic illustration of introduction of the intravascular balloon catheter of FIG. 1 to a region in the coronary vasculature.
Figure 13:
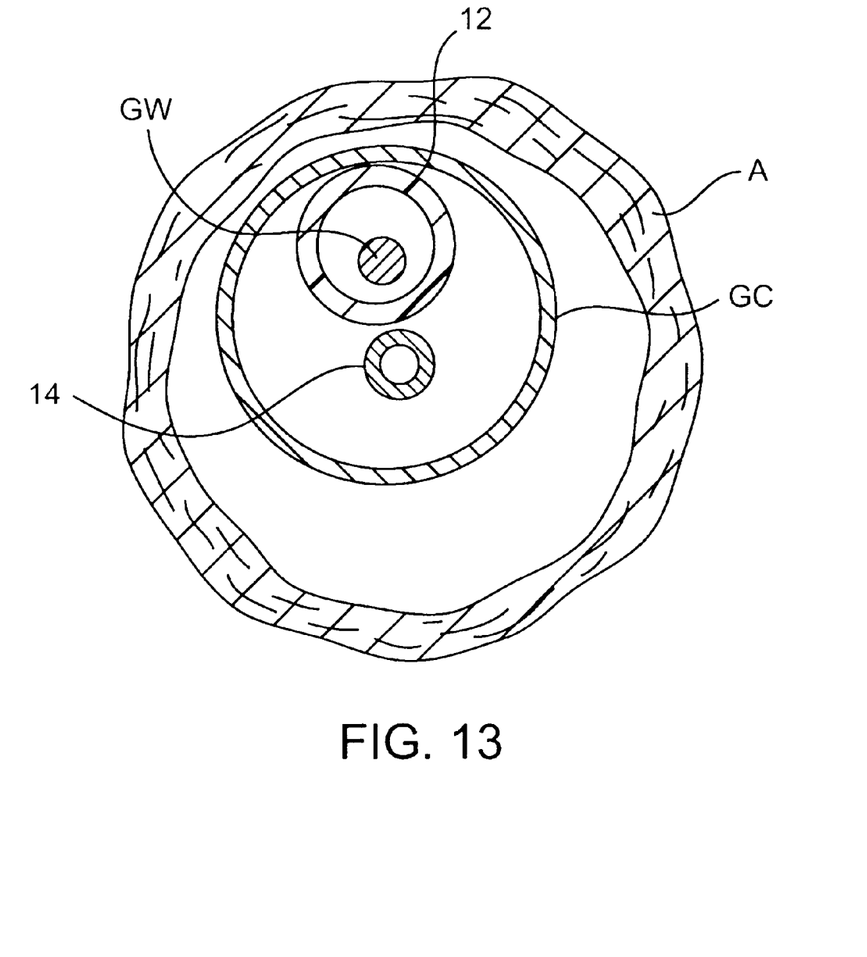
FIG. 13 is a cross-sectional view taken along line 13—13 of FIG. 12.

Referring now to FIGS. 12,13, and 14A–14H, use of the intravascular balloon catheter 10 for performing balloon angioplasty followed by stent treatment of a coronary artery and a patient P will be described. A balloon catheter 10 may be introduced to a target site in the coronary vasculature through a guide catheter GC and over a guidewire GW, as illustrated in FIGS. 12 and 13. The intravasculature balloon catheter 10 is introduced in through the guiding catheter GC via hemostatic valve and sheath (not shown) and through the femoral artery A to the coronary vasculature over the aortic arch AA.

Figure 13A:
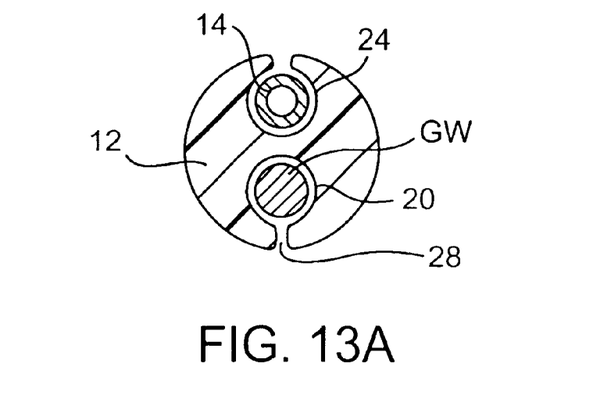
FIG. 13A shows an alternative cross-sectional view similar to FIG. 13.

Alternatively, as shown in FIG. 13A, the tubular-catheter body 12 may comprise an axial slot 24 for removably receiving the inflation tube 14, and the guidewire lumen 20 may be axially slit 28 to permit removal and/or introduction of the guidewire.

Figure 14A:
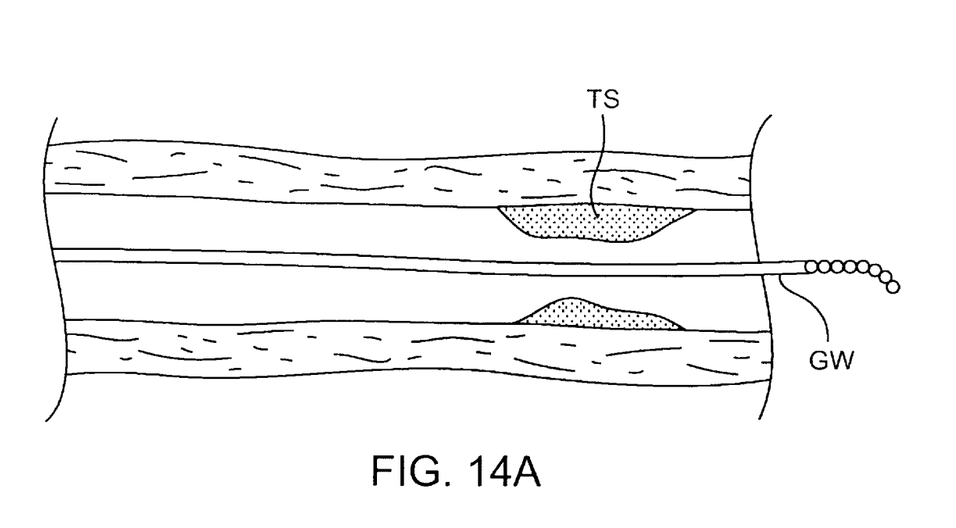
FIGS. 14A–14H illustrate the steps in an exemplary method preformed using the intravascular catheter of FIG. 1 in accordance with the principles of the present invention.
Figure 14B:
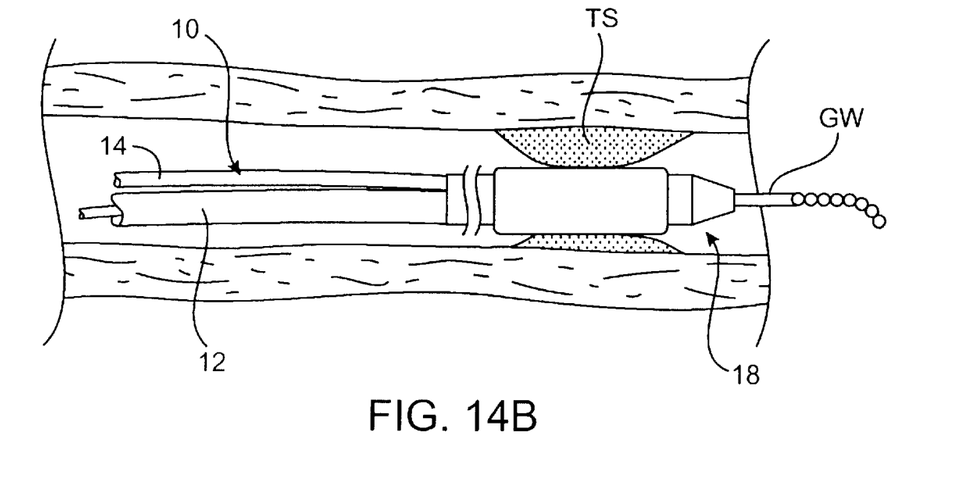

As shown in FIG. 14A, the guidewire GW will usually be positioned at the target site TS, typically a region of stenosis to be treated by balloon angioplasty. Usually, the balloon catheter 10 and guidewire GW will be introduced together with the guidewire being periodically extended forward of the distal end 18 of the catheter until the target site is reached, as shown in FIG. 14B.

Figure 14C:
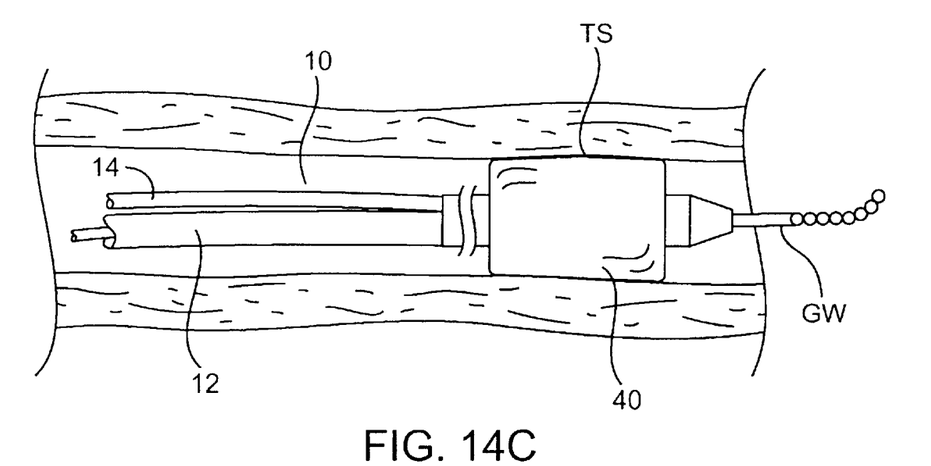
Figure 14D:
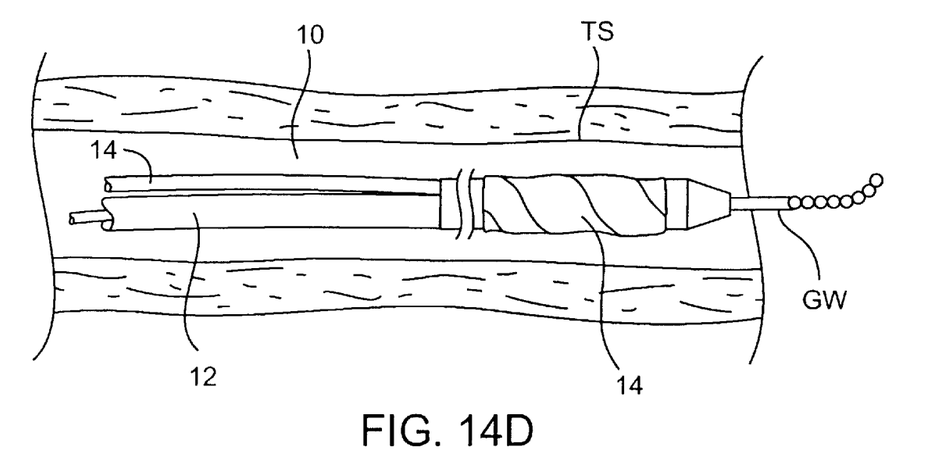
Figure 14E:
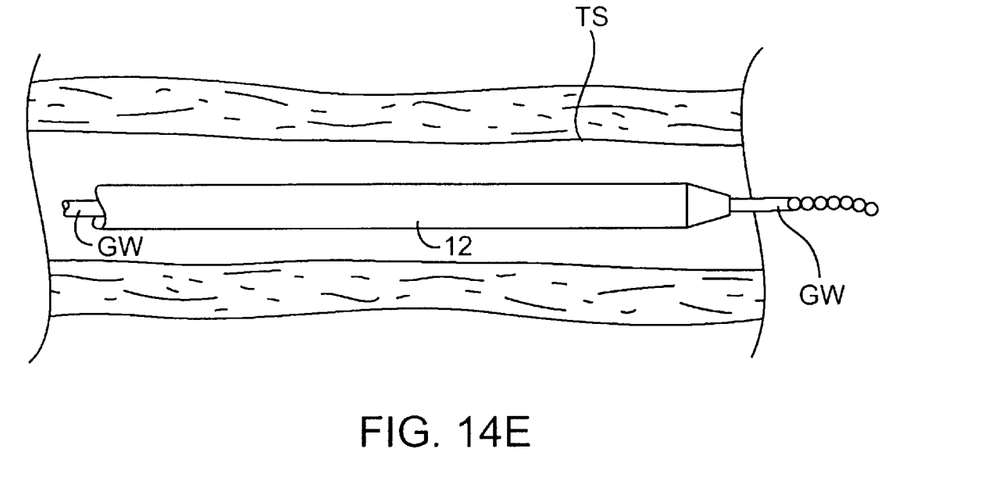
Figure 14F:
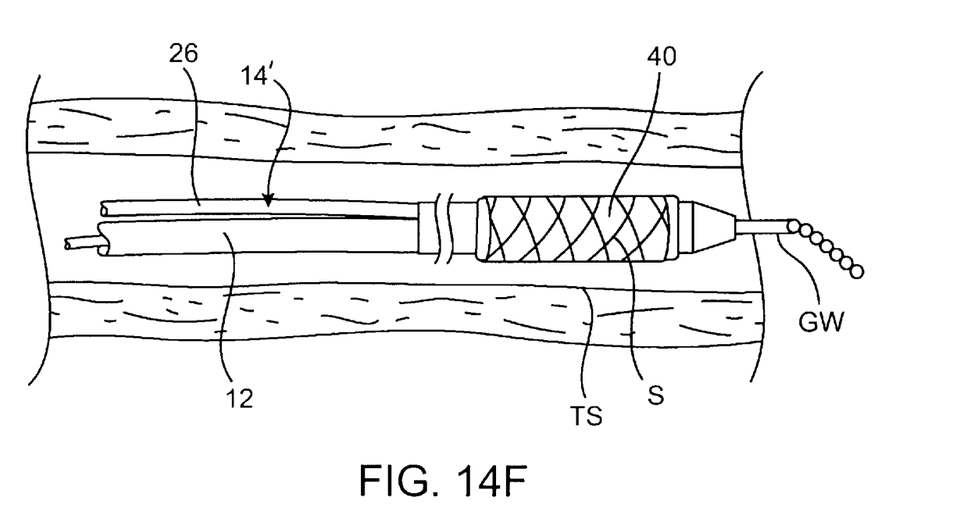
Figure 14G:
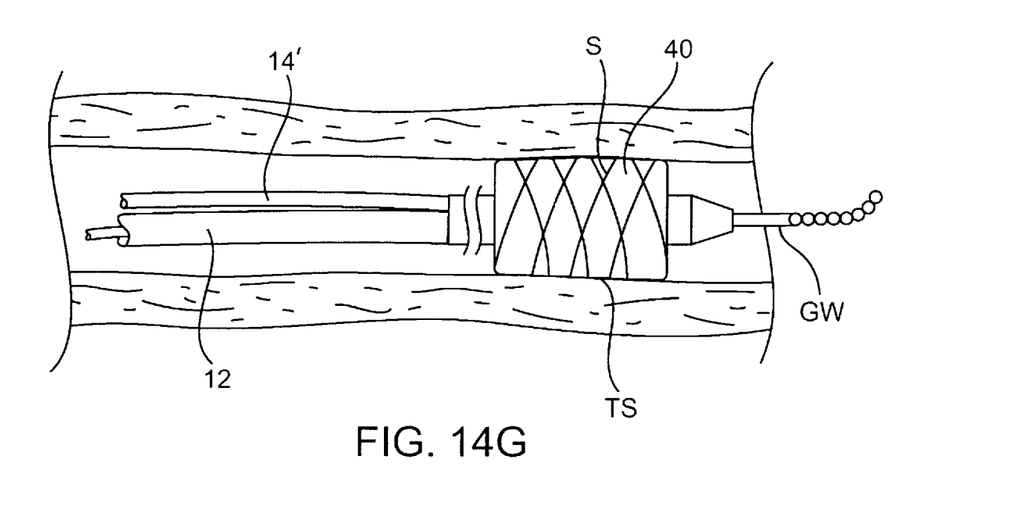

Once at the target site, TS the balloon 40 is inflated as shown in FIG. 14C, in order to expand the occlusion at the target site TS. After the balloon angioplasty treatment is completed, the balloon 40 will be deflated, as shown in FIG. 14D, with guidewire GW remaining in place. The balloon structure 14 may then be removed from over the tubular catheter body 12, as shown in FIG. 14E, again with the guidewire GW remaining in place. A second balloon structure 14' may then be introduced over the catheter body 12 by pushing the balloon assembly 34 distally using the inflation tube 26 (FIG. 14F). After the balloon assembly 34 is in place, a stent S which is in place over the balloon assembly may be deployed by inflating balloon 40, as shown in FIG. 14G. At all times, the guidewire GW has remained in place, while the balloon structures 14 and 14' have been exchanged over the tubular catheter body 12.

Figure 14H:
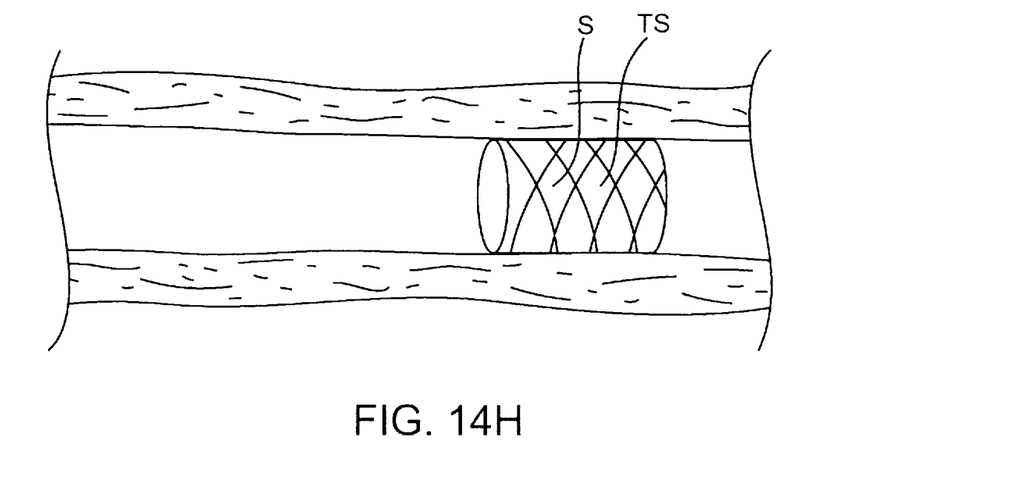

After the stent S has been properly deployed, balloon 40 may be deflated and the catheter 10 removed. Removal of catheter 10 may be effected simultaneously with removal of the guidewire, i.e. the catheter, including both the tubular catheter body 12 and balloon structure 14', may be withdrawn simultaneously with the guidewire. Alternatively, the balloon structure 14' could be removed first, with the guidewire GW and the tubular catheter body 12 then being withdrawn simultaneously. As still a further alternative, the guidewire GW may be left in place by withdrawing the tubular catheter body 12 over guidewire GW. When the guidewire GW is a short guidewire, it will be advantageous to provide means in the catheter body for pulling the guidewire from the guidewire lumen as the tubular catheter body is withdrawn. For example, the tubular catheter body could include an axial split in order to permit withdrawal of the guidewire as the tubular catheter body is withdrawn. This allows the treating physician to maintain a hold on the guidewire as the tubular catheter body is withdrawn. Alternatively, catheter body could have a splitable structure which permnits the catheter body to be peeled part as the catheters withdrawn. Peeling apart catheter also permits the treating physician to have access to the guidewire at all times of the withdrawal of the catheter body 12. Again, the procedure, the stent S will remain in place within the target site, as illustrated in FIG. 14H.

Figure 15:
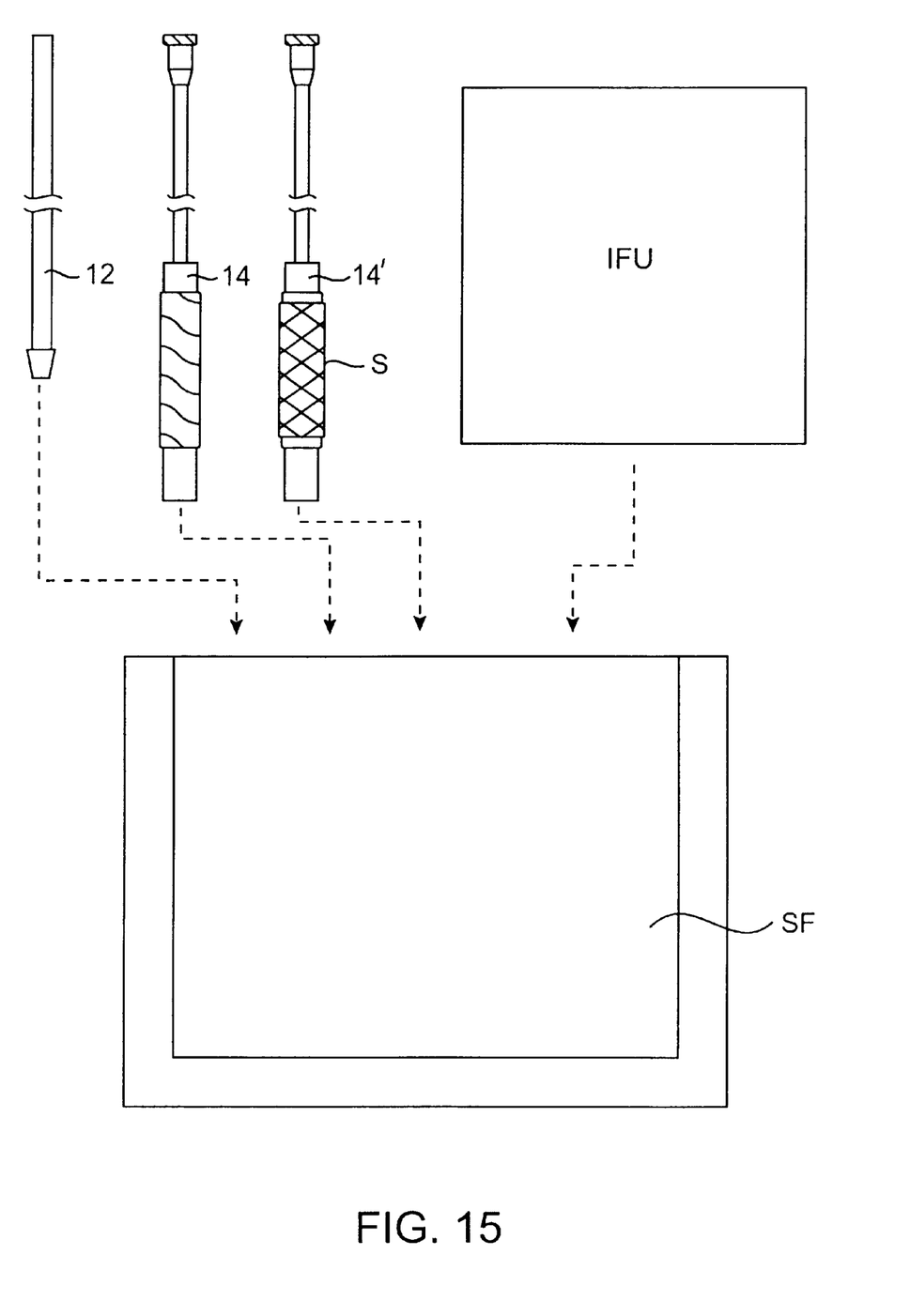
FIGS. 15 illustrates a kit in accordance with the principles of the present invention.

The system components of the balloon catheters of the present invention may be configured as kits as shown in FIG. 15. The kits may comprise any one or more of the system components together with instructions for use IFU and/or sterile packaging SP. Usually, the kits will comprise at least a tubular catheter body, e.g. tubular catheter body 12, and one balloon structure, e.g. balloon structure 14. Optionally, the kit will include at least a second balloon structure 14, and the second structure may carry a balloon expansible or other vascular prosthesis, e.g. an stent S. The IFU may set forth any of the methods described herein.

Although the foregoing invention has been described in some detail by way of illustration and example, for purposes of clarity of understanding, it will be obvious that certain changes and modifications may be practiced within the scope of the appended claims.

What is claimed is:

1. An intravascular balloon catheter comprising:
   a tubular catheter body having a proximal end, a distal end, and a guidewire lumen therebetween; and
   a first balloon structure having a passage which is slidably receivable over the proximal end of the tubular catheter body, wherein the tubular catheter body has an inflation lumen which mates with an inflation port on the balloon structure when the balloon structure is disposed near the distal end of the tubular catheter body.

2. An intravascular balloon catheter as in claim 1, wherein the balloon structure comprises an inflation tube extending proximally from the balloon when the balloon is disposed n ear the distal end of the tubular catheter body.

3. An intravascular balloon catheter as in claim 2, wherein the inflation tube has sufficient column strength to advance the balloon structure over the tubular catheter body.

4. An intravascular balloon catheter as in claim 1, wherein the balloon structure comprises a deployment shaft extending proximally from the balloon structure when the balloon structure is disposed near the distal end of the tubular catheter body.

5. An intravascular balloon catheter as in claim 1, wherein the tubular catheter body is substantially free from structure at the proximal end which would interfere with passage of the balloon structure over the proximal end of the tubular catheter body.

6. An intravascular balloon catheter as in claim 1, further comprising an expandable vascular prosthesis disposed over the first balloon structure.

7. An intravascular balloon catheter system comprising a balloon catheter as in claim 1, further comprising a second balloon structure having a passage which is slidably receivable over the tubular catheter body.

8. An intravascular balloon catheter system as in claim 7, further comprising an expandable vascular prosthesis disposed over the second balloon structure.

9. An intravascular balloon catheter as in claim 1, wherein the tubular catheter body is axially slit over at least a portion of the length of the guidewire lumen.

10. An intravascular balloon catheter as in claim 9, wherein the axial slit removably receives the guidewire.

11. An intravascular balloon catheter as in claim 1, wherein the tubular catheter body has a length in the range from 100 cm to 200 cm, an outer diameter in the range from 1 F to 10 F, and a guidewire lumen diameter in the range from 0.3 mm to 2 mm.

12. An intravascular balloon catheter as in claim 11, wherein the balloon structure further comprises an inner sleeve having an inflatable balloon disposed over an outer surface of the inner sleeve, wherein a passage is formed axially in the inner sleeve to removably receive the tubular catheter body.

13. An intravascular balloon catheter as in claim 12, wherein the inner sleeve has a length in the range form 3 cm to 50 cm and the inflatable balloon has a length in the range from 1 cm to 5 cm.

14. An intravascular balloon catheter as in claim 1, further comprising a hub which is removably attachable to the proximal end of the tubular catheter body.

* * * * *